United States Patent [19]

Dugan

[11] Patent Number: Plant 6,128

[45] Date of Patent: Mar. 15, 1988

[54] EUONYMUS PLANT NAMED THUNDERBOLT

[75] Inventor: Thomas F. Dugan, Perry, Ohio

[73] Assignee: Dugan Nurseries, Incorporated, Perry, Ohio

[21] Appl. No.: 833,053

[22] Filed: Feb. 25, 1986

[51] Int. Cl.[4] ..... A01H 5/00
[52] U.S. Cl. ..... Plt./63
[58] Field of Search ..... Plt./63

*Primary Examiner*—Robert E. Bagwill

*Attorney, Agent, or Firm*—Schwartz, Jeffery, Schwaab, Mack, Blumenthal & Evans

[57] ABSTRACT

The new cultivar Thunderbolt is especially characterized by its broadleaf evergreen foliage which has pronounced irregular yellow centers that cover an area of the leaf around the midvein, with the leaves inside the plant being of the same variegated color as leaves on the stem tips, thereby giving the plant as a whole a distinctive and striking dark green appearance with jagged stripes and spots of yellow accenting the foliage. The plant is further characterized by its profuse display of yellow-green flowers in May.

2 Drawing Figures

1

The present invention comprises a new and distinctive cultivar of Euonymus plant, botanically known as *Euonymus fortunei*, and hereinafter referred to by the cultivar name Thunderbolt.

Thunderbolt is a sport of the Euonymus plant known by the cultivar name Sunspot, disclosed in U.S. Plant Pat. No. 4,340. Thunderbolt was discovered by me in Perry, Ohio, in a cultivated area in which plants of the parent cultivar Sunspot were being grown. Thunderbolt was discovered in the form of a branch of the parent cultivar in which the foliage showed diminished variegation. The sport was also observed due to the unique showing of a smaller golden spot in the center of the green leaf, and by the stems of the plant being striped green and yellow in color. Continued observation of the sport, as well as the subsequent asexually reproduced plants thereof, convinced me that the sport is both new and distinct from the parent cultivar, as well as from all other cultivars of Euonymus plants of which I am aware.

The following unique combination of characteristics have been repeatedly observed and serve to distinguish Thunderbolt as a new and distinct cultivar:

1. A distinctive variegation pattern in which a yellow spot or jagged stripe covers an area of the leaf near the midvein surrounded by the normal green foliage color.
2. Unusually showy striped yellow and green stem color.
3. Elongated stem internodes.
4. Improved vigor compared to the parent cultivar, and especially compared to other variegated Euonymus cuiltivars.
5. An attractive upright and spreading plant shape.
6. Larger and thicker leaves than the parent cultivar.
7. Attractive, showy, and profuse yellow-green flowers borne in May, and the ability to bear flowers at a young plant age.

Asexual reproduction of Thunderbolt by me commencing in November, 1982 in Perry, Ohio by cuttings has established that the foregoing characteristics and distinctions come true to form and are established and transmitted through succeeding generations.

The accompanying photographic drawings illustrate, on sheet 1, a typical two year old specimen plant of the new cultivar in perspective view.

2

Sheet 2 comprises a close-up photograph of a group of branches of Thunderbolt showing in more detail the leaf and stem characteristics. The color in the photographs is as nearly true as possible in color renditions of this type. The photographs were taken outdoors in Lansing, Mich. between 1:00 and 3:00 p.m. in mid-winter when the cultivar was not in flower.

The following is a detailed description of the new cultivar, with color values being referenced to The Royal Horticultural Society Colour Chart, except where general color terms of ordinary dictionary significance are used. The color values were taken in Ashtabula, Ohio at approximately 10:00 a.m. on Jan. 8, 1986.

Form: Upright, spreading and somewhat open; fast growing; taller and broader than the parent cultivar Sunspot.

Growth:

*Two year plants.*—Height, from about 18 to 24 inches; breadth, from about 18 to 24 inches.

*Mature plants.*—Height, from about 3 to 4 feet; breadth, from about 3 to 4 feet.

Hardiness: Good winter hardiness is evidenced by the fact that plants grown outdoors have withstood winter temperatures of U.S.D.A. hardiness zone 5 with little protection, and U.S.D.A. hardiness zone 4 with some wind protection.

Stems (branchlets): Smooth, dull; color, intense yellow, Group 10B-C with plentiful green streaking 147-A on older, more mature stems. Long internodes from 10 to 50 mm. Coarsely textured; from 5 to 10 mm. in diameter. Stripes of woody brown bark develop on more mature stems. Occasional aerial roots.

Axillary buds: Small, elongate, conical, and less than 5 mm. long.

Foliage:

*Type.*—Broadleaf evergreen, petioled, opposite.

*Shape.*—Ovate to elliptic.

*Petioles.*—Length, 5 to 15 mm.; color green 147-B.

*Size of leaf.*—Length from 3 to 6 cm.; breadth from 2 to 3 cm.

*Leaf texture.*—Heavy compared to parent plant Sunspot; leathery, smooth, upper surface glossy; lower surface dull.

*Veining.*—On leaf underside only the midrib is visibly veined; on upper surface, veins are slightly raised and visible on green sectors of the leaf.

*Leaf margins.*—Crenate, serrate, flat.

*Color.*—Center of leaf, upper side vivid Yellow 10B-C, covers thin jagged stripe along the midvein of the leaf, with areas of stronger concentration toward Yellow 10-B. Center of leaf, under side, Yellow Group 10 between B and C. Remainder of leaf, upper side Green Group 139B. Edges of leaf, under side, Green Group 139B-C. Shape and size of central yellow stripe is variable from a tiny yellow stripe at the base of the petiole to a stripe that extends almost to the leaf tip, with short fingers of yellow color following some of the lateral veins. On newly expanding leaves, all colors tend towards a lighter green, but darken quickly so that new leaves when fully expanded are very close in color to the oldest leaves on a given plant.

Flower: Groups of 1 to 5 or more composite flowers may bloom from terminal axillary buds in early to Mid-May in Ohio. Flowers are born on peduncles 2 to 3 cm. long; flower heads composite with 16 florets, each floret consisting of 4 short pointed sepals below 4 petals and stamens with a pistil in the center. The stamens and pistil are of equal length from 4 to 6 mm. The petals are round, about 4 mm. in diameter. All flower parts are vivid yellow-green 150 between B and C and provide a showy contrast to the dark green leaf color. The large number and tiny size of the flowers provide a downy soft texture to the overall plant during the flowering period. The profuse covering of large bunches of composite flowers occurs even on young plants, and the display may continue into early June.

I claim:

1. A new and distinct cultivar of Euonymus plant known by the cultivar name Thunderbolt, as illustrated and described, and characterized particularly as to uniqueness by the combined characteristics of profuse yellow-green flower display in May; upright, spreading and vigorous habit of growth; good winter hardiness; large thick broadleaf evergreen foliage having pronounced narrow yellow centers with broad dark green margins of irregular depth with the leaves inside the plant being of the same variegated color as the stem tips, thereby giving the plant as a whole a distinctive and dark green appearance accented by irregular bolt shaped stripes of yellow variegation.

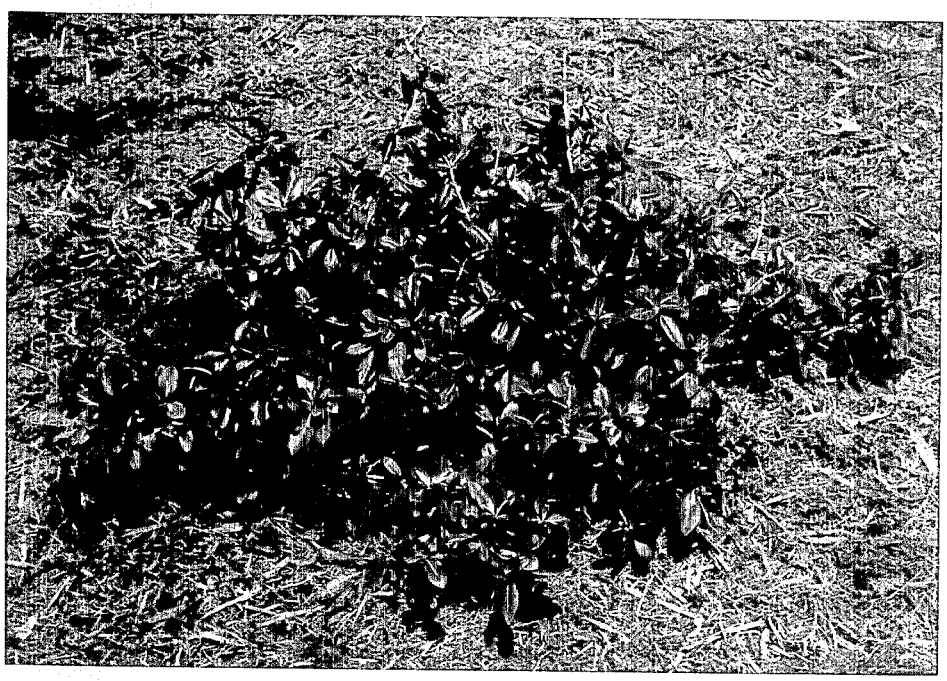

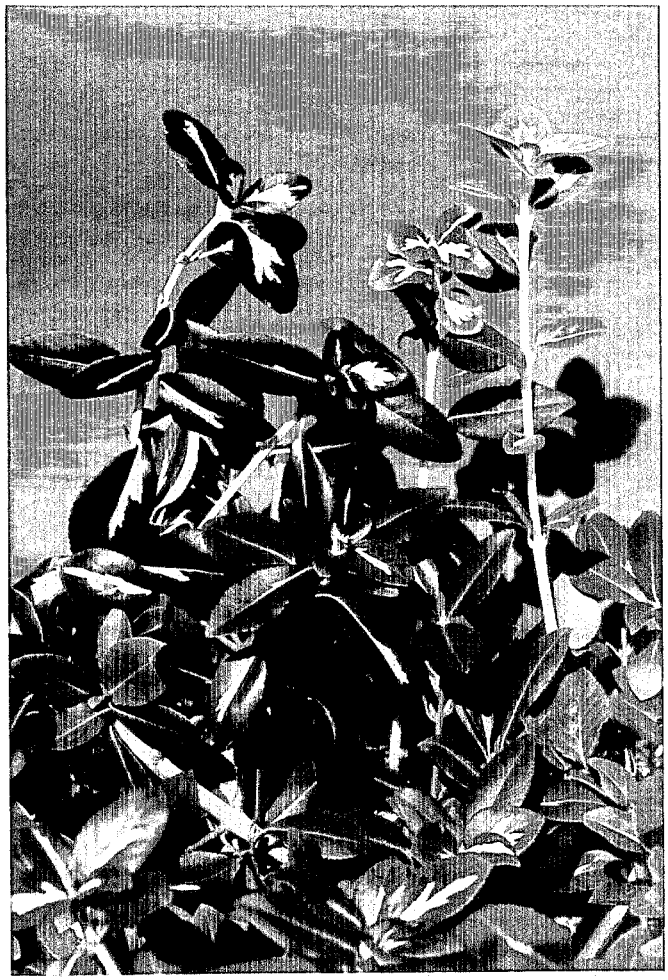

* * * * *